United States Patent [19]

Beller et al.

[11] Patent Number: 5,599,523
[45] Date of Patent: Feb. 4, 1997

[54] ECHO CONTRAST AGENT

[75] Inventors: Klaus-Dieter Beller; Rudolf Linder, both of Konstanz, Germany

[73] Assignee: BYK Gulden Lomberg Chemische Fabrik GmbH, Konstanz, Germany

[21] Appl. No.: 347,206

[22] Filed: Nov. 22, 1994

Related U.S. Application Data

[63] Continuation of Ser. No. 78,189, filed as PCT/EP92/00012, Jan. 4, 1992 published as WO92/11873, Jul. 23, 1992.

[30] Foreign Application Priority Data

Jan. 9, 1991 [DE] Germany .......................... 41 00 470.1

[51] Int. Cl.$^6$ ..................................................... A61K 49/00
[52] U.S. Cl. .......................... 424/9.52; 424/9.5; 424/9.51
[58] Field of Search ................................ 424/9, 450, 9.5, 424/9.51, 9.52; 128/662.02

[56] References Cited

U.S. PATENT DOCUMENTS

| | | | |
|---|---|---|---|
| 4,466,442 | 8/1984 | Hilmann et al. ......................... | 128/653 |
| 4,900,540 | 2/1990 | Ryan et al. ................................ | 424/9 |
| 4,902,500 | 2/1990 | Jansen et al. ............................. | 424/78 |
| 5,271,928 | 12/1993 | Schneider et al. ...................... | 424/9.51 |

FOREIGN PATENT DOCUMENTS 0318081  5/1989  European Pat. Off. .

OTHER PUBLICATIONS

"Contrast Echocardiography of the Left Heart by Intravenous Injection of Perfluorochemical Emulsion" *Journal of Cardiography*, 13:1021–1028, 1983 Matsuda et al.—Japan.
"Contrast Echocardiography of the Left Heart by Intravenous Injection of Perfluorochemical Emulsion" Journal of Cardiography 13: 1021–1028, 1983—English translation.
World Patents Index Latest, Section Ch, Week 8421 (1984).
File Server Stn Karlsruhe, File Biosis Abstract No. 92:8782, (1991).
Matsuda et al., Journal of Cardiography, 13(4), 1021–1028, (1983). (Abstract Only).

*Primary Examiner*—Brian M. Burn
*Assistant Examiner*—Mary C. Cebulak
*Attorney, Agent, or Firm*—Jacobson, Price, Holman & Stern, PLLC

[57] ABSTRACT

An aqueous preparation for receiving and stabilising micro gas bubbles for use as echo contrast media containing polyoxyethylene/polyoxypropylene polymers and negatively charged phospholipids, which is suitable for demonstration of the left ventricle, is indicated.

24 Claims, 1 Drawing Sheet

FIG. 1
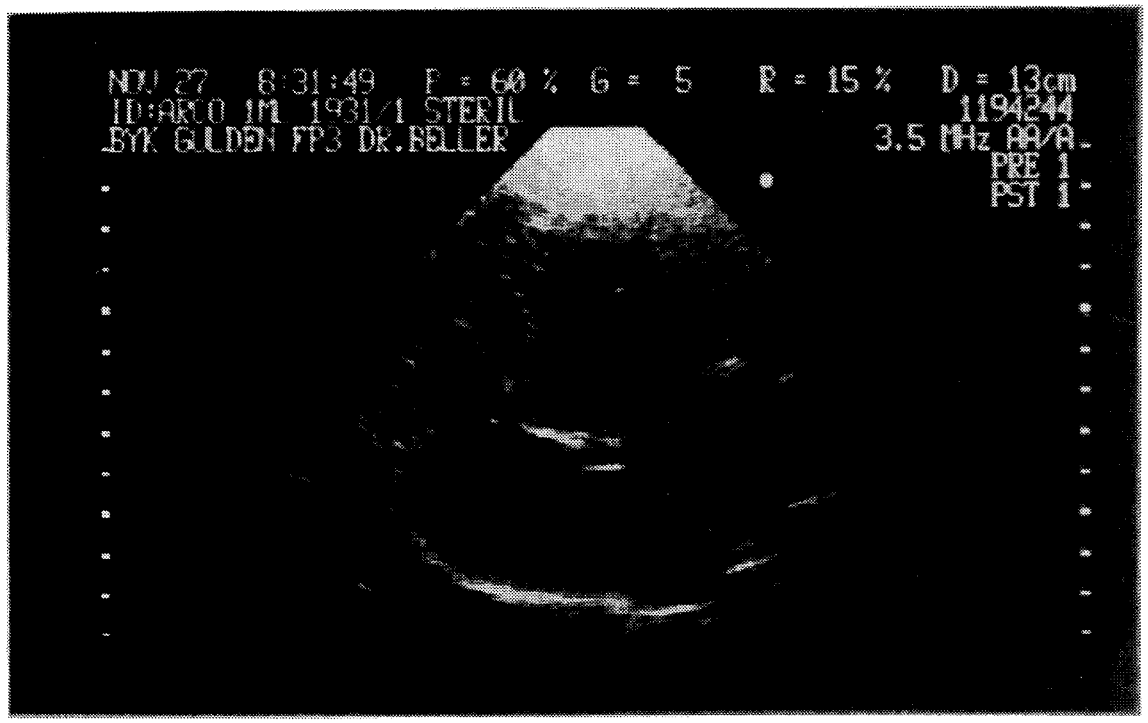
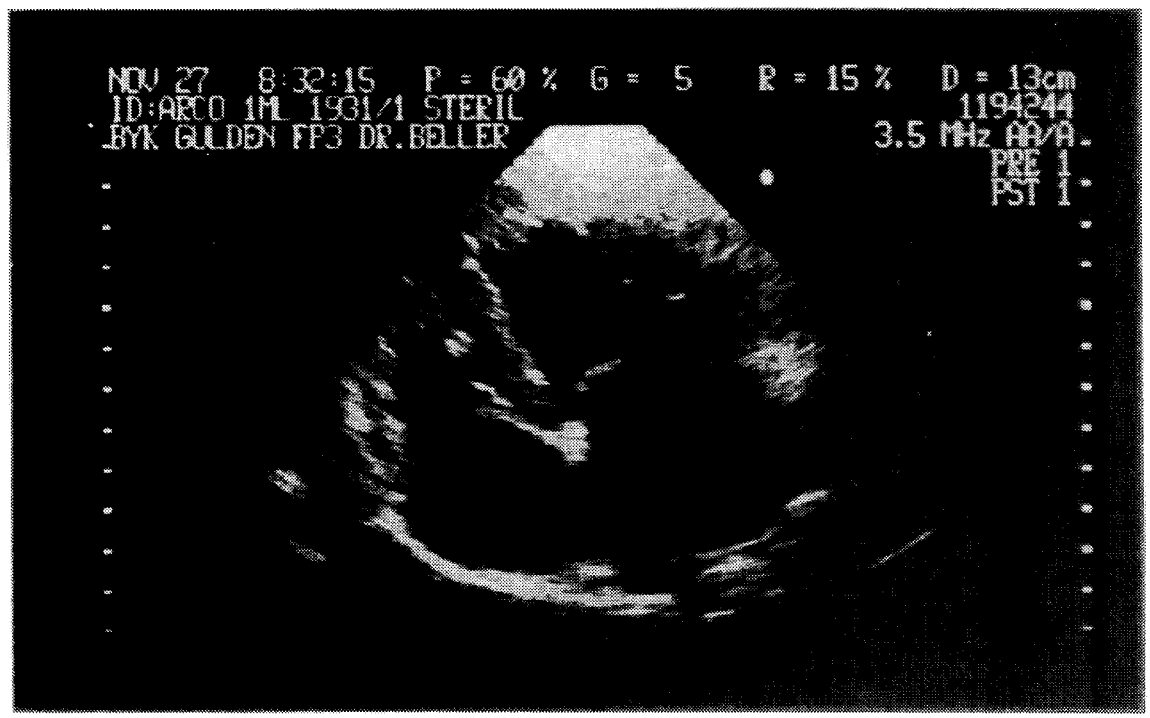
FIG. 2

ECHO CONTRAST AGENT

This application is a continuation of application Ser. No. 08/078,189, filed Jun. 21, 1993, now abandoned, which is a 371 of PCT/EP92/00012, filed Jan. 4, 1992.

FIELD OF THE INVENTION

The invention relates to an aqueous preparation for receiving and stabilising micro gas bubbles for use as echo contrast media.

PRIOR ART

Since ultrasound is highly reflected by gas bubbles suspended in liquids, there was an early proposal to use aqueous preparations which contain stabilised micro gas bubbles as contrast media for ultrasonic diagnosis. Micro gas bubbles can be stabilised in aqueous preparations by reducing the surface tension, that is to say by adding suitable surfactants.

It is indicated in EP-B-0 077 752 that aqueous solutions which contain a surfactant or a mixture of surfactants and, in addition, a viscosity-increasing substance have advantageous contrast-generating properties. Indicated as suitable surfactants are, inter alia, non-ionic lecithins and lecithin fractions, and polyoxyethylene/polyoxpropylene polymers. The preparations indicated in the six preparation examples of EP-B-0 077 752 each contain as surfactant a polyoxyethylene/polyoxypropylene polymer and as viscosity-increasing substance glucose or dextran or the polyoxyethylene/polyoxypropylene polymer itself. Repetition of the preparation examples has shown that the contrast-generating action is unsatisfactory. Thus, the preparations of EP-B-0 077 752 are unsuitable for demonstrations of the left ventricle.

It has now been found, surprisingly, that aqueous preparations which, besides polyoxyethylene/polyoxypropylene polymers, contain negatively charged phospholipids are outstandingly suitable for receiving and stabilising micro gas bubbles.

SUMMARY OF THE INVENTION

The invention therefore relates to aqueous preparations for receiving and stabilising micro gas bubbles for use as echo contrast media containing polyoxyethylene/polyoxypropylene polymers and negatively charged phospholipids.

Further subject-matter is evident from the claims.

Preferred polyoxyethylene/polyoxypropylene polymers are those with an average molecular weight of 8,350 to 14,000. Polyoxyethylene/polyoxypropylene polymers are also called poloxamers and are commercially available, for example, under the proprietary name Pluronics® (Wyandotte Chemicals Corp.). The preparations according to the invention contain 0.1 to 10%, preferably 1 to 5%, of polyoxyethylene/polyoxypropylene polymers. The content of negatively charged phospholipids is from 0.01 to 5%, preferably 0.5 to 2%. Percentage data in each case relate to weight/volume.

Suitable negatively charged phospholipids are phosphatidylglycerols, phosphatidylinositols, phosphatidylethanolamines and phosphatidylserines and the lyso forms thereof. By lyso forms of the negatively charged phospholipids are meant negatively charged phospholipids which contain only one acyl radical. Lyso forms of the negatively charged phospholipids in which the acyl group is bonded to the oxygen of the carbon atom 1 of the glycerol molecule are preferred. Particularly preferred negatively charged phospholipids are dipalmitoylphosphatidylglycerol (DPPG) and distearoylphosphatidylglycerol (DSPG), and distearoylphosphatidylglycerol (DSPG) is very particularly preferred.

The preparations according to the invention are distinguished from those of the prior art in that echo contrast media containing micro gas bubbles can be produced with little mechanical effort and, because of their great stability, generate a long-lasting contrast and moreover are outstandingly suitable for demonstration of the left ventricle. It should be particularly emphasised that the preparations according to the invention are excellently suitable for the demonstration of internal surface structures because the micro gas bubbles apparently adhere well to surfaces and thus generate informative contrast even after the micro gas bubbles which are located in the lumen of vessels have been flushed out. This makes it possible, for example, to demonstrate more clearly the dynamics of the heart even after the contrast medium has been washed out.

The preparation of the preparations according to the invention is not difficult and can take place by introducing the individual components together or successively into water and dissolving, if necessary with heating and stirring. Sterilisation is also possible if required, for example by heat sterilisation.

Glycerol, mannitol and ammonium salts of amino acids, preferably glycine, have proved particularly well suited for adjusting the isotonicity of the preparations according to the invention.

The micro gas bubbles are generated in a manner known per se and expediently only shortly before administration to the patients to be investigated. If, for example, the preparation according to the invention is provided in a vial, the solution can be drawn up together with the required amount of air into a conventional syringe and injected again into the vial through a narrow needle with the highest possible pressure. If necessary, the drawing up and expulsion from the syringe is repeated several times. It is also possible as an alternative to force the preparations according to the invention backwards and forwards between two syringes via a connector with a narrow cross-section or a mixing chamber inserted between the two syringes. The latter method leads to particularly informative ultrasonic images with, at the same time, a further increase in productivity.

Suitable gases for generating the micro gas bubbles are all physiologically tolerated gases. The preparations according to the invention are converted into a foam with 0.01 to 0.1, preferably with 0.04 to 0.06, ml of gas per 1 ml. They are preferably administered intravenously after generation of the micro gas bubbles. Depending on the purpose for which the preparations according to the invention are used, 1 to 20 ml, preferably 2 to 8 ml, and particularly preferably 5 ml are administered.

It should be particularly emphasised that lower doses of the preparations according to the invention are possible because of their increased productivity compared with the prior art.

EXAMPLES 1. 3.0 g of polyoxyethylene/polyoxypropylene polymer with an average molecular weight of 8,400 (Pluronic®F68), 1.0 g of dipalmitoylphosphatidylglycerol (DPPG) and 3.6 g of glycerol are introduced into 80 ml of water. The mixture is heated to about 80° C. and stirred until complete dissolution has taken place. After cooling, the volume is made up to 100 ml with distilled water.

2. The process is carried out as in Example 1 with the difference that 1.0 g of soya phosphatidylglycerol (supplied by Lucas Meyer, Hamburg) is used in place of DPPG.

3. 1.1 g of glycine are introduced into 80 ml of water. A pH of 6 to 7 is adjusted with dilute ammonia. 3.0 g of polyoxyethylene/polyoxypropylene polymer with an average molecular weight of 8,400 (Pluronic®F68) and 1.0 g of DPPG are added to the solution. The mixture is heated to about 80° C. and stirred until complete dissolution has taken place. After cooling, the volume is made up to 100 ml with distilled water.

4. The process is carried out as in Example 3 with the difference that 1.0 g of soya phosphatidylglycerol (supplied by Lucas Meyer) is used in place of DPPG.

5. 4.0 g of polyoxyethylene/polyoxypropylene polymer (Poloxamer 188, Pluronic®F68), 1.0 g of distearoylphosphatidylglcyerol and 5.4 g of mannitol are introduced into 80 ml of water. The mixture is heated to about 80° C. and stirred until dissolution is complete. After cooling, the volume is made up to 100 ml with distilled water.

COMPARATIVE EXPERIMENTS

The investigations were carried out on conscious male beagle dogs (18.2–30.5 kg body weight). The dogs received in each case 5 ml, administered i.v., of the contrast medium preparations described below:

A: An infusion solution, containing 35 g of crosslinked polypeptides per 1,000 ml, for plasma replacement (Haemaccel® supplied by Behringwerke)

B: Echovist® (echo contrast medium supplied by Schering)

C: An aqueous solution containing 4% by weight poloxomer 188 (Pluronic®F68) and 4% by weight glucose (Example 1 in EP 0 077 752)

D: An aqueous solution containing 2% by weight poloxamer and 4% by weight glucose (Example 2 in EP 0 077 752)

E: An aqueous solution containing 1% by weight poloxamer and 4% by weight glucose (Example 3 in EP 0 077 752)

F: Preparation according to the invention from Example 5

Solutions A, C, D, E and F are drawn up without air into a first syringe. This syringe is then connected by the free end to a mixing chamber which contains 0.18 ml of air and is firmly connected to a second syringe. Immediately before administration, the solutions are pumped out of the first syringe through the mixing chamber into the second syringe and back again five times.

The commercially available contrast medium B is prepared as instructed in the pack insert.

The echocardiographic ultrasonic scans were carried out with a Sonoscope 4 ultrasonic instrument with mechanical head at 3.5 MHz. The videoprints of the resulting ultrasonic images were evaluated for the intensity of contrast by densitometry. The densitometer used (Gretag D182) determines the changes in the brightness in 100 steps in the range from 0.00 to 2.50 density units. The calibration is carried out using the DIN 16536 calibration card (calibration reference) provided by the manufacturer, where the lightest white is assigned the value 1.64 and the darkest black is assigned the value 0.00. The average of four individual determinations on an area of 1 cm×1 cm gives the value for the administered preparation for each animal.

The results obtained are shown in the table which follows.

| 5 ml | right ventricle | | | left ventricle | | |
|---|---|---|---|---|---|---|
| | | Intensity | | | Intensity | |
| | Contrast | max | 10 sec | Contrast | max | 10 sec |
| A | yes | 1.18 | 0.86 | no | 0.00 | 0.00 |
| B | yes | 1.09 | 0.65 | no | 0.00 | 0.00 |
| C | yes | 1.20 | 0.78 | no | 0.00 | 0.00 |
| D | yes | 1.23 | 0.87 | no | 0.00 | 0.00 |
| E | yes | 1.22 | 0.93 | no | 0.00 | 0.00 |
| F | yes | 1.19 | 0.82 | yes | 0.78 | 0.72 |

Intensity in Density Units (DU)

It is evident from the results that the echo contrast media according to the invention enter the lungs, in contrast to the echo contrast media of the prior art, and are therefore excellently suited for diagnosis in the left ventricle. The utilisability of ultrasonic imaging in cardiac diagnosis is considerably extended by the echo contrast media according to the invention.

In addition, it has been found that the micro bubbles of the echo contrast media according to the invention apparently have a considerable affinity for the internal surfaces of vessels and cavities in the body. The consequence of this is that the outlines of vessels and cavities are demonstrated much better and therefore more informatively than was possible with contrast media of the prior art. It is particularly advantageous in this connection that this great improvement in the demonstration of the surfaces of vessels and cavities even persists when the lumen of the vessel or cavity is already free of echo contrast medium. This surprising contrast of surfaces can be utilised, for example, for observation of the endocardium.

FIGS. 1 and 2 depict the result of an experiment to demonstrate this novel contrast of surface structures.

FIG. 1 shows the echocardiographic image of the endocardium of a conscious beagle dog in the so-called four-chamber view immediately before appearance of the first contrast after administration of 1 ml of echo contrast medium from Example 1.

FIG. 2 shows the endocardium of the animal after the echo contrast medium has already been washed out of the heart again.

It is evident from comparison of the two figures that an unexpected marking of the endocardium, which signifies a large gain in information for diagnostic purposes, is possible with echo contrast media according to the invention.

We claim:

1. An aqueous preparation useful for receiving and stabilising micro gas bubbles for use as echo contrast media and containing polyoxyethylene/polyoxypropylene polymer and anionic phospholipid.

2. An aqueous preparation of claim 1 which comprises, as sole essential components, water, polyoxyethylene/polyoxypropylene polymer and anionic phospholipid, optionally in combination with isotonicity adjusting component means.

3. A preparation according to claim 2, wherein the the polyoxyethylene/polyoxypropylene polymer comprises from 0.1 to 10% (weight/volume).

4. A preparation according to claim 3, wherein the polyoxyethylene/polyoxypropylene polymer comprises from 1 to 5% (weight/volume).

5. A preparation according to claim 1, containing phosphatidylglycerol, phosphatidylinositol, phosphatidylethanolamine or phosphatidylserine as the anionic phospholipid.

6. A preparation according to claim 5, containing distearoylphosphatidylglycerol as the anionic phospholipid.

7. A preparation according to claim 1, containing the anionic phospholipid in an amount of from 0.01 to 5% (weight/volume).

8. A preparation according to claim 1, containing 3% (weight/volume) of polyoxyethylene/polyoxypropylene polymer with an average molecular weight of 8,400 and 1% (weight/volume) of distearoylphosphatidylglycerol.

9. A preparation according to claim 1, wherein the anionic phospholipid is present as lyso form.

10. A process for the preparation of an aqueous preparation for receiving and stabilising micro bubbles for use as echo contrast media, which comprises dissolving in water polyoxyethylene/polyoxypropylene polymer together with a anionic phospholipid and customary auxiliaries for achieving isotonicity.

11. In an aqueous echo contrast medium containing polyoxyethylene/polyoxypropylene polymer, the improvement wherein the polymer is in admixture with anionic phospholipid.

12. An aqueous preparation of claim 2 which consists essentially of polyoxyethylene/polyoxypropylene polymer and anionic phospholipid dissolved in water.

13. An aqueous preparation of claim 2 useful for receiving and stabilizing micro gas bubbles for use as echo contrast medium and containing polyoxyethylene/polyoxypropylene polymer and anionic phospholipid;

the polymer having an average molecular weight of from 8,350 to 14,000; and the anionic phospholipid being a member selected from the group consisting of a phosphatidylglycerol, a phosphatidylinositol, a phosphatidylethanolamine and a phosphatidylserine.

14. An aqueous preparation according to claim 13 containing from 0.1 to 10 percent (weight/volume) of the polyoxyethylene/polyoxypropylene polymer.

15. An aqueous preparation according to claim 14 containing from 0.01 to 5 percent (weight/volume) of the anionic phospholipid.

16. An aqueous preparation according to claim 15 wherein the anionic phospholipid is a phosphatidylglycerol.

17. An aqueous preparation according to claim 15 wherein the anionic phospholipid is a phosphatidylinositol.

18. An aqueous preparation according to claim 15 wherein the anionic phospholipid is a phosphatidylethanolamine.

19. An aqueous preparation according to claim 15 wherein the anionic phospholipid is a phosphatidylserine.

20. An aqueous preparation of claim 1 which is suitable for demonstration of the left ventricle.

21. A preparation according to claim 1, wherein the polyoxyethylene/polyoxypropylene polymer has an average molecular weight of from 8,350 to 14,000.

22. An echo contrast medium which is an aqueous preparation of claim 1 in intimate admixture with stabilized micro gas bubbles.

23. An echo contrast medium which is an aqueous preparation of claim 21 in intimate admixture with stabilized micro gas bubbles.

24. An echo contrast medium of claim 22, having great stability and being produced with little mechanical effort.

* * * * *